United States Patent [19]

Wenderoth et al.

[11] Patent Number: 4,956,387
[45] Date of Patent: Sep. 11, 1990

[54] SUBSTITUTED HYDRAZONES AND FUNGICIDES CONTAINING THESE COMPOUNDS

[75] Inventors: Bernd Wenderoth, Lampertheim; Siegbert Brand, Weinheim; Franz Schuetz, Ludwigshafen; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 310,651

[22] Filed: Feb. 15, 1989

[30] Foreign Application Priority Data

Mar. 3, 1988 [DE] Fed. Rep. of Germany ....... 3806874

[51] Int. Cl.$^5$ ............................................. A01N 37/00
[52] U.S. Cl. ..................... 514/522; 514/535; 514/539; 560/21; 560/35; 562/435; 562/440; 558/414; 558/415
[58] Field of Search .................... 560/35, 21; 562/435, 562/440; 558/415, 414; 514/522, 535, 539

[56] References Cited

U.S. PATENT DOCUMENTS

| 4,163,062 | 7/1979 | Clark et al. | 424/324 |
| 4,163,793 | 8/1979 | Clark et al. | 424/275 |
| 4,212,868 | 7/1980 | Clark et al. | 424/263 |

FOREIGN PATENT DOCUMENTS

| 1768136 | 4/1968 | Fed. Rep. of Germany . |
| 1768137 | 4/1968 | Fed. Rep. of Germany . |
| 63-313758 | 12/1988 | Japan ........................ 560/35 |
| 1333027 | 4/1972 | United Kingdom . |
| 2192883 | 1/1988 | United Kingdom ................. 560/35 |

Primary Examiner—Bruce Gray
Attorney, Agent, or Firm—Oblon, Spivak, McClelland, Maier & Neustadt

[57] ABSTRACT

Substituted hydrazones of the formula I

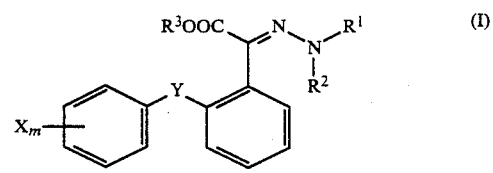

where
$R^1$, $R^2$ and $R^3$ are hydrogen or alkyl,
X (m=1 to 5) is halogen, cyano, trifluoromethyl, nitro, alkyl, alkoxy, substituted or unsubstituted phenyl, substituted or unsubstituted phenoxy, substituted or unsubstituted benzyloxy or hydrogen, and
Y is methyleneoxy, oxymethylene, ethylene, ethenylene, ethynylene, carboxymethylene, carbonylamino, methyleneamino or oxygen, and fungicides containing these compounds.

8 Claims, No Drawings

SUBSTITUTED HYDRAZONES AND FUNGICIDES CONTAINING THESE COMPOUNDS

The present invention relates to novel hydrazone derivatives, their preparation and their use as fungicides.

It is known that N-tridecyl-2,6-dimethylmorpholine can be used as a fungicide (DE-1 164 152). However, its action is inadequate in some cases.

We have found that novel hydrazone derivatives of the formula I

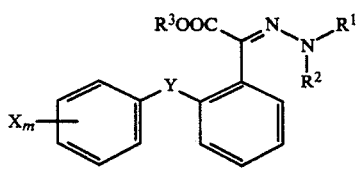

where $R^1$, $R^2$ and $R^3$ are identical or different and are each hydrogen or alkyl of 1 to 5 carbon atoms, the radicals X (where m is from 1 to 5) are identical or different substituents from the group consisting of halogen, cyano, trifluoromethyl, nitro, $C_1$–$C_4$-alkyl, $C_1$–$C_4$-alkoxy, unsubstituted or substituted phenyl, unsubstituted or substituted phenoxy, unsubstituted or substituted benzyloxy and hydrogen, and Y is methyleneoxy, oxymethylene, ethylene, ethenylene, ethynylene, carboxymethylene, carbonylamino, methyleneamino or oxygen, not only have a very good fungitoxic action but are also very well tolerated by plants.

Because of the C=N double bond, some of the compounds of the formula I are obtained in the preparation as E/Z isomer mixtures, which can be separated into the individual components in a conventional manner, for example by crystallization or chromatography. The invention embraces both the individual isomeric compounds and their mixtures.

$R^1$ and $R^2$ are each preferably hydrogen or $C_1$–$C_5$-alkyl, such as methyl, ethyl, n-propyl, isopropyl, n-butyl, sec-butyl, isobutyl, tert-butyl, n-pentyl or neopentyl.

$R^3$ is preferably hydrogen or $C_1$–$C_4$-alkyl, such as methyl, ethyl, isopropyl or n-butyl.

m is preferably 1, 2 or 3.

X is preferably hydrogen, 2-fluoro, 3-fluoro, 4-fluoro, 2-chloro-6-fluoro, 2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert-butyl, 2,4-dimethyl, 2,6-dimethyl, 2,4,6-trimethyl, 2-methoxy-4-methyl, 4-methoxy-2-methyl, 2-methoxy, 3-methoxy, 4-methoxy, 4-ethoxy, 4-isopropoxy, 2-trifluoromethyl, 3-trifluoromethyl, 4-trifluoromethyl, 2-cyano, 4-cyano, 3-nitro, 4-nitro, 4-phenyl, 4-benzyloxy, 4-phenoxy, halophenoxy, such as 4-(2-chlorophenoxy) or 4-(2,4-dichlorophenoxy), $C_1$–$C_4$-alkylphenoxy, such as 4-(2-methyphenoxy), 3-benzyloxy, halobenzyloxy, such as 3-(2-chlorobenzyloxy), 3-(2,4-dichlorobenzyloxy), 3-(2-fluorobenzyloxy) or 3-(4-bromobenzyloxy), $C_1$–$C_4$-alkylbenzyloxy, such as 3-(2-methylbenzyloxy), 3-phenoxy, 3-(2-chlorophenoxy), 3-(2,4-dichlorophenoxy), 3-(2-fluorophenoxy), 3-(4-bromophenoxy) or 3-(2-methylphenoxy), and Y is preferably —CH$_2$O—, —OCH$_2$—, —CH$_2$—CH$_2$—, —CH=CH—, —C≡C—, —CO$_2$—CH$_2$—, —CO—NH—, —CH$_2$—NH— or O.

The novel compounds can be prepared by reacting an α-ketocarboxylic ester of the formula II

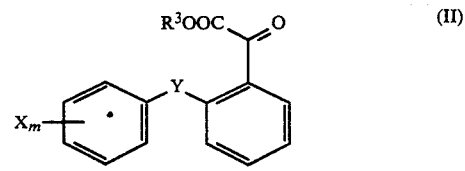

where $X_m$, Y and $R^3$ have the abovementioned meanings, with a substituted hydrazine of the general formula III, where $R^1$ and $R^2$ have the abovementioned meanings

in the presence of a protic acid (eg. hydrochloric acid) in a solvent (eg. methanol) (cf. H. Neunhoeffer, M. Neunhoeffer and W. Litzius, Liebigs Ann. Chem. 722 (1969), 29–37).

The α-ketocarboxylic esters of the formula II can be prepared by reacting the corresponding Grignard compounds, for example

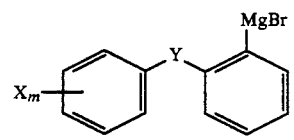

with imidazolides of the formula IV (J. S. Nimitz and H. S. Mosher, J. Org. Chem. 46 (1981), 211–213)

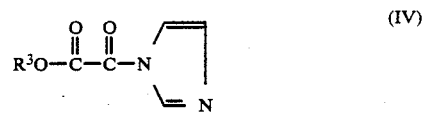

where X, m, Y and $R^3$ have the abovementioned meanings.

Another preparation process for α-ketocarboxylic esters of the formula II (where Y is —CO—NH— or —CH$_2$—NH) is, for example, the following:

Isatin is reacted with an unsubstituted or substituted benzoyl halide or an unsubstituted or substituted benzyl halide in the presence of a base, for example sodium hydride, in a solvent, for example N,N-dimethylformamide, to give an N-substituted isatin of the formula V or VI (cf. G. Tacconi, P. P. Righetti, G. Desimoni, J. prakt. Chem. 315 (1973), 339–334)

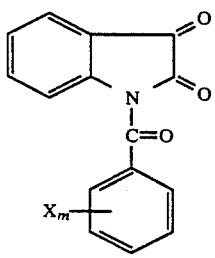
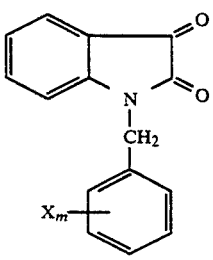

N-benzoylisatin (V)   N-benzylisatin (VI)

where X and m have the abovementioned meanings. Heating in R³—OH, where R³ has the abovementioned meanings, in the presence of a Lewis acid or protic acid, for example titanium tetrachloride or HCl, gives the α-ketocarboxylic esters of the formula II:

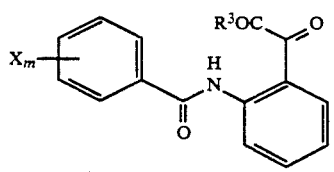

(II), Y = —CO—NH—

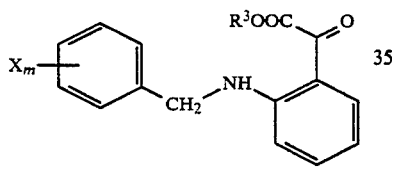

(II), Y = —CH₂—NH—

Another preparation process for α-ketocarboxylic esters of the formula II (where Y is —CO₂—CH₂—) is, for example, the following:

Methyl α-(2-bromomethylphenyl)-β-methoxyacrylate (cf. DE-3 545 318, DE-3 545 319 and DE-3 620 860) in a solvent

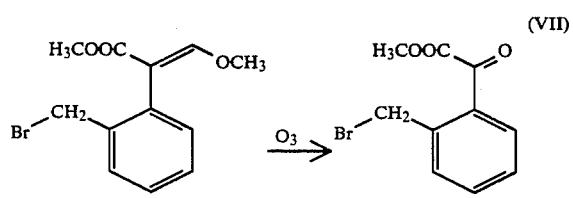

(eg. methanol) is subjected to ozonolysis (cf. Bailey, Ozonation in Organic Chemistry, Academic Press, N.Y., 1982), and the novel compound methyl 2-(bromomethyl)-phenylglyoxylate VII is obtained. This compound is a useful intermediate for the preparation of the novel hydrazones.

By reacting compound VII with a known carboxylate of the formula VIII

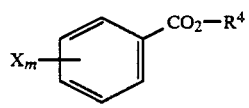

(VIII)

where X and m have the abovementioned meanings and $R^4$ is, for example, sodium or potassium, in a solvent, for example N,N-dimethylformamide (cf. Synthesis 1975, 805-807), the novel α-ketocarboxylic esters of the formula II (where Y is —CO₂—CH₂—) are obtained.

By reacting compound VII with a phenol derivative of the formula IX (cf. Houben-Weyl, Methoden der organischen Chemie VI/3, 54 et seq. (1965))

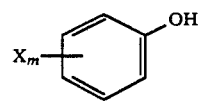

(IX)

where X and m have the abovementioned meanings, in a solvent (eg. methanol) in the presence of a base, eg. sodium carbonate, the α-ketocarboxylic esters of the formula II (where Y is —OCH₂—) are obtained.

Another preparation process for methyl 2-(bromomethyl)-phenylglyoxylate VII is, for example, the following:

Bromination of the known α-ketocarboxylic ester of the formula X (cf. for example J. M. Photis, Tetrahedron Lett. 1980, 3539)

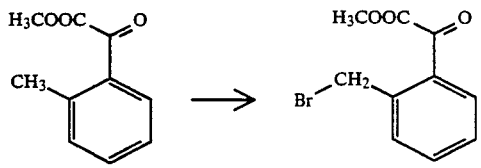

(X)   (VII)

with bromine in a solvent, eg. tetrachloromethane, with or without exposure to a light source (for example a 300 W mercury vapor lamp) or bromination with N-bromosuccinimide (Horner and Winkelmann, Angew. Chem. 71 (1959), 349) leads to the compound VII.

The preparation of the compounds of the formulae I, II and VII is illustrated by the following Examples: 1. Preparation of methyl 2-(bromomethyl)-phenylglyoxylate 1.1 2.85 g (10 millimoles) of methyl α-(2-bromomethylphenyl)-β-methoxyacrylate are dissolved in 30 ml of 1:1 dichloromethane/ethanol at −78° C. Ozone is passed into the stirred solution for one hour until a pale blue coloration is obtained (ozone generator: Fischer OZ 501, 60 l of O₂/h).

1.24 g (20 millimoles) of dimethyl sulfide are then added, and the mixture is allowed to warm up to room temperature (20° C.) overnight. The mixture is then poured onto a 1:1:1 mixture of diethyl ether, n-hexane and water. The organic phase is separated off, dried over sodium sulfate and evaporated down. The abovementioned compound is obtained as a yellow oil.

1.2 5.34 g (30 millimoles) of methyl 2-methylphenylglyoxylate and 5.34 g (30 millimoles) of N-bromosuccinimide in 1,000 ml of tetrachloromethane are exposed for one hour to a 300 W mercury vapor lamp. Then, the or-ganic phase is washed once with water and 3 times with sodium bicarbonate solution, dried over sodium sulfate/sodium carbonate and evaporated down, and the crude pro-duct is chromatographed over silica gel using 1:9 methyl tert-butyl ether/n-hexane. 3.8 g (49%) of the abovementioned compound are obtained as a yellow oil.

The compound VII has the following physical properties:

¹H-NMR (CDCl₃): δ=3.97 (s, 3H), 4.90 (s, 2H), 7.4–7.8 (m, 4H).

IR (film): 2955, 1740, 1689, 1435, 1318, 1207, 999 cm⁻¹.

2. Methyl 2-(benzoylamino)-phenylglyoxylate

2.1 Preparation of N-benzoylisatin.

14.7 g (0.10 mole) of isatin (dissolved in 100 ml of N,N-dimethylformamide) are added to 2.6 g (0.11 mole) of sodium hydride in 100 ml of N,N-dimethylformamide, while stirring. After the mixture has been stirred for one hour at room temperature, 14.1 g (0.10 mole) of benzoyl chloride are added dropwise at 0° C. Stirring is then continued for 10 minutes at 0° C. and the mixture is poured onto ice. The precipitate which separates out is filtered off under suction and dried to give 20 g (80%) of N-benzoylisatin as yellow crystals.

IR (film): 2470, 1776, 1746, 1687, 1605, 1465, 1336, 1287, 761.

2.2 Preparation of methyl 2-(benzoylamino)-phenylglyoxylate.

13 g (52 millimoles) of N-benzoylisatin together with one drop of concentrated hydrochloric acid in 100 ml of methanol are refluxed for eight hours. After cooling, the mixture is evaporated down in a rotary evaporator to give 14 g (95%) of the abovementioned α-ketocarboxylic ester as yellow crystals having the following physical properties:

¹H-NMR (CDCl₃): δ=4.03 (s, 3H), 7.22 (m, 1H), 7.55 (m, 3H), 7.76 (m, 3H), 8.10 (d, 2H), 9.05 (d, 1H), 12.10 (s, 1H).

IR (film): 3315, 1733, 1647, 1583, 1535, 1450, 1297, 1210, 1159, 694.

3. Preparation of methyl 2-(benzyloxy)-phenylglyoxylate 0.1 mole of a Grignard compound prepared from 1-benzyloxy-2-bromobenzene and magnesium turnings in tetrahydrofuran is slowly added dropwise to 14.6 g (95 millimoles) of methyloxalylimidazole in tetrahydrofuran under nitrogen at −50° C. The mixture is allowed to reach room temperature (20° C.) slowly over a period of 4 hours. It is poured onto ice water and extracted several times with ether. The combined ether phases are washed neutral and dried. The solvent is evaporated off and the product is then brought to crystallization with n-pentane. 16 g (62%) of colorless crystals of the abovementioned compound were obtained.

¹H-NMR (CDCl₃): δ=3.35 (s, 3H), 5.07 (s, 2H), 7.05 (m, 2H), 7.40 (m, 5H), 7.55 (m, 1H), 7.90 (m, 1H).

4. Preparation of N-methylhydrazone of methyl 2-(benzyloxy)-phenylglyoxylate (compound No. 1 in the Table)

13.5 g (50 millimoles) of methyl 2-(benzyloxy)-phenylglyoxylate, 2.3 g (50 millimoles) of methylhydrazine and 25 ml of 2N HCl in 250 ml of methanol are stirred for 3 days at room temperature. The mixture is evaporated down, the residue is taken up in ethyl acetate and the solution is washed with dilute sodium bicarbonate solution and then with water. It is dried over sodium sulfate and then evaporated down. The crude product is chromatographed over a silica gel column (9:1 cyclohexane/ethyl acetate). 2.7 g (18%) of the above-mentioned hydrazone are obtained as a yellow oil.

¹H-NMR (CDCl₃): δ=3.25 (s, 3H), 3.55 (s, 3H), 5.05 (s, 2H), 6.85–7.05 (m, 2H), 7.2–7.4 (m, 6H).

The compounds below can be prepared in a similar manner.

TABLE

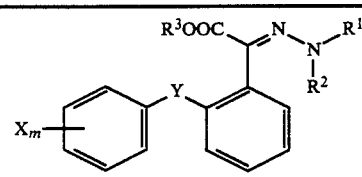

(I)

| Comp. no. | $X_m$ | Y | $R^1$ | $R^2$ | $R^3$ | M.p.(°C.) IR(cm⁻¹) |
|---|---|---|---|---|---|---|
| 1 | H | —CH₂O— | CH₃ | H | CH₃ | 3265, 1671, 1489, 1434, 1320, 1221, 1159, 759 |
| 2 | 2-F | —CH₂O— | CH₃ | H | CH₃ | |
| 3 | 3-F | —CH₂O— | CH₃ | H | CH₃ | |
| 4 | 4-F | —CH₂O— | CH₃ | H | CH₃ | |
| 5 | 2-Cl, 6-F | —CH₂O— | CH₃ | H | CH₃ | |
| 6 | 2-Cl | —CH₂O— | CH₃ | H | CH₃ | 3320, 1681, 1546, 1437, 1327, 1256, 1162, 756 |
| 7 | 3-Cl | —CH₂O— | CH₃ | H | CH₃ | |
| 8 | 4-Cl | —CH₂O— | CH₃ | H | CH₃ | |
| 9 | 2-Br | —CH₂O— | CH₃ | H | CH₃ | |
| 10 | 3-Br | —CH₂O— | CH₃ | H | CH₃ | |
| 11 | 4-Br | —CH₂O— | CH₃ | H | CH₃ | |
| 12 | 2,4-Cl₂ | —CH₂O— | CH₃ | H | CH₃ | |
| 13 | 2,6-Cl₂ | —CH₂O— | CH₃ | H | CH₃ | |
| 14 | 3,5-Cl₂ | —CH₂O— | CH₃ | H | CH₃ | |
| 15 | 2,4,6-Cl₃ | —CH₂O— | CH₃ | H | CH₃ | |
| 16 | 2-Cl, 4-CH₃ | —CH₂O— | CH₃ | H | CH₃ | |
| 17 | 2-CH₃, 4-Cl | —CH₂O— | CH₃ | H | CH₃ | |
| 18 | 2-CH₃ | —CH₂O— | CH₃ | H | CH₃ | |
| 19 | 3-CH₃ | —CH₂O— | CH₃ | H | CH₃ | |
| 20 | 4-CH₃ | —CH₂O— | CH₃ | H | CH₃ | |

TABLE-continued (I)

$$R^3OOC-C(=N-NR^1R^2)-Ar$$

where Ar is 2-(X_m-C_6H_{4-m}-Y)-phenyl

| Comp. no. | $X_m$ | Y | $R^1$ | $R^2$ | $R^3$ | M.p.(°C.) IR(cm$^{-1}$) |
|---|---|---|---|---|---|---|
| 21 | 4-C$_2$H$_5$ | —CH$_2$O— | CH$_3$ | H | CH$_3$ | |
| 22 | 4-i-C$_3$H$_7$ | —CH$_2$O— | CH$_3$ | H | CH$_3$ | |
| 23 | 4-t-C$_4$H$_9$ | —CH$_2$O— | CH$_3$ | H | CH$_3$ | |
| 24 | 2,4-(CH$_3$)$_2$ | —CH$_2$O— | CH$_3$ | H | CH$_3$ | |
| 25 | 2,6-(CH$_3$)$_2$ | —CH$_2$O— | CH$_3$ | H | CH$_3$ | |
| 26 | 2,4,6-(CH$_3$)$_3$ | —CH$_2$O— | CH$_3$ | H | CH$_3$ | |
| 27 | 2-OCH$_3$, 4-CH$_3$ | —CH$_2$O— | CH$_3$ | H | CH$_3$ | |
| 28 | 4-OCH$_3$, 2-CH$_3$ | —CH$_2$O— | CH$_3$ | H | CH$_3$ | |
| 29 | 2-OCH$_3$ | —CH$_2$O— | CH$_3$ | H | CH$_3$ | |
| 30 | 3-OCH$_3$ | —CH$_2$O— | CH$_3$ | H | CH$_3$ | 113–115; 3315, 1675, 1545, 1436, 1328, 1270, 1230, 1160, 1040, 768 |
| 31 | 4-OCH$_3$ | —CH$_2$O— | CH$_3$ | H | CH$_3$ | |
| 32 | 4-OC$_2$H$_5$ | —CH$_2$O— | CH$_3$ | H | CH$_3$ | |
| 33 | 4-O-i-C$_3$H$_7$ | —CH$_2$O— | CH$_3$ | H | CH$_3$ | |
| 34 | 2-CF$_3$ | —CH$_2$O— | CH$_3$ | H | CH$_3$ | |
| 35 | 3-CF$_3$ | —CH$_2$O— | CH$_3$ | H | CH$_3$ | |
| 36 | 4-CF$_3$ | —CH$_2$O— | CH$_3$ | H | CH$_3$ | |
| 37 | 2-CN | —CH$_2$O— | CH$_3$ | H | CH$_3$ | |
| 38 | 4-CN | —CH$_2$O— | CH$_3$ | H | CH$_3$ | |
| 39 | 3-NO$_2$ | —CH$_2$O— | CH$_3$ | H | CH$_3$ | |
| 40 | 4-NO$_2$ | —CH$_2$O— | CH$_3$ | H | CH$_3$ | |
| 41 | 4-C$_6$H$_5$ | —CH$_2$O— | CH$_3$ | H | CH$_3$ | |
| 42 | H | —OCH$_2$— | CH$_3$ | H | CH$_3$ | 3275, 2955, 1673, 1598, 1528, 1496, 1219, 1153, 755 |
| 43 | 2-F | —OCH$_2$— | CH$_3$ | H | CH$_3$ | |
| 44 | 3-F | —OCH$_2$— | CH$_3$ | H | CH$_3$ | |
| 45 | 4-F | —OCH$_2$— | CH$_3$ | H | CH$_3$ | |
| 46 | 2-Cl, 6-F | —OCH$_2$— | CH$_3$ | H | CH$_3$ | |
| 47 | 2-Cl | —OCH$_2$— | CH$_3$ | H | CH$_3$ | 3310, 2950, 1707, 1485 1245, 1158, 750 |
| 48 | 3-Cl | —OCH$_2$— | CH$_3$ | H | CH$_3$ | |
| 49 | 4-Cl | —OCH$_2$— | CH$_3$ | H | CH$_3$ | |
| 50 | 2-Br | —OCH$_2$— | CH$_3$ | H | CH$_3$ | |
| 51 | 3-Br | —OCH$_2$— | CH$_3$ | H | CH$_3$ | |
| 52 | 4-Br | —OCH$_2$— | CH$_3$ | H | CH$_3$ | |
| 53 | 2,4-Cl$_2$ | —OCH$_2$— | CH$_3$ | H | CH$_3$ | |
| 54 | 2,6-Cl$_2$ | —OCH$_2$— | CH$_3$ | H | CH$_3$ | |
| 55 | 3,5-Cl$_2$ | —OCH$_2$— | CH$_3$ | H | CH$_3$ | |
| 56 | 2,4,6-Cl$_3$ | —OCH$_2$— | CH$_3$ | H | CH$_3$ | |
| 57 | 2-Cl, 4-CH$_3$ | —OCH$_2$— | CH$_3$ | H | CH$_3$ | |
| 58 | 2-CH$_3$, 4-Cl | —OCH$_2$— | CH$_3$ | H | CH$_3$ | |
| 59 | 2-CH$_3$ | —OCH$_2$— | CH$_3$ | H | CH$_3$ | |
| 60 | 3-CH$_3$ | —OCH$_2$— | CH$_3$ | H | CH$_3$ | |
| 61 | 4-CH$_3$ | —OCH$_2$— | CH$_3$ | H | CH$_3$ | 3320, 2920, 1684, 1508, 1437, 1330, 1233, 1165, 1014, 760 |
| 62 | 4-C$_2$H$_5$ | —OCH$_2$— | CH$_3$ | H | CH$_3$ | |
| 63 | 4-i-C$_3$H$_7$ | —OCH$_2$— | CH$_3$ | H | CH$_3$ | |
| 64 | 4-t-C$_4$H$_9$ | —OCH$_2$— | CH$_3$ | H | CH$_3$ | |
| 65 | 2,4-(CH$_3$)$_2$ | —OCH$_2$— | CH$_3$ | H | CH$_3$ | |
| 66 | 2,6-(CH$_3$)$_2$ | —OCH$_2$— | CH$_3$ | H | CH$_3$ | |
| 67 | 2,4,6-(CH$_3$)$_3$ | —OCH$_2$— | CH$_3$ | H | CH$_3$ | |
| 68 | 2-OCH$_3$, 4-CH$_3$ | —OCH$_2$— | CH$_3$ | H | CH$_3$ | |
| 69 | 4-OCH$_3$, 2-CH$_3$ | —OCH$_2$— | CH$_3$ | H | CH$_3$ | |
| 70 | 2-OCH$_3$ | —OCH$_2$— | CH$_3$ | H | CH$_3$ | |
| 71 | 3-OCH$_3$ | —OCH$_2$— | CH$_3$ | H | CH$_3$ | |
| 72 | 4-OCH$_3$ | —OCH$_2$— | CH$_3$ | H | CH$_3$ | |
| 73 | 4-OC$_2$H$_5$ | —OCH$_2$— | CH$_3$ | H | CH$_3$ | |
| 74 | 4-O-iC$_3$H$_7$ | —OCH$_2$— | CH$_3$ | H | CH$_3$ | |
| 75 | 2-CF$_3$ | —OCH$_2$— | CH$_3$ | H | CH$_3$ | |
| 76 | 3-CF$_3$ | —OCH$_2$— | CH$_3$ | H | CH$_3$ | |
| 77 | 4-CF$_3$ | —OCH$_2$— | CH$_3$ | H | CH$_3$ | |
| 78 | 2-CN | —OCH$_2$— | CH$_3$ | H | CH$_3$ | |
| 79 | 4-CN | —OCH$_2$— | CH$_3$ | H | CH$_3$ | |
| 80 | 3-NO$_2$ | —OCH$_2$— | CH$_3$ | H | CH$_3$ | |
| 81 | 4-NO$_2$ | —OCH$_2$— | CH$_3$ | H | CH$_3$ | |
| 82 | 4-C$_6$H$_5$ | —OCH$_2$— | CH$_3$ | H | CH$_3$ | |
| 83 | H | —CH=CH— | CH$_3$ | H | CH$_3$ | |
| 84 | 2-F | —CH=CH— | CH$_3$ | H | CH$_3$ | |
| 85 | 3-F | —CH=CH— | CH$_3$ | H | CH$_3$ | |
| 86 | 4-F | —CH=CH— | CH$_3$ | H | CH$_3$ | |

TABLE-continued

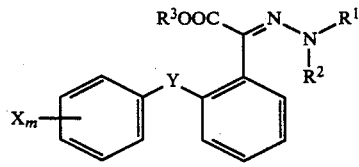

(I)

| Comp. no. | $X_m$ | Y | $R^1$ | $R^2$ | $R^3$ | M.p.(°C.) IR(cm$^{-1}$) |
|---|---|---|---|---|---|---|
| 87 | 2-Cl, 6-F | —CH=CH— | CH$_3$ | H | CH$_3$ | |
| 88 | 2-Cl | —CH=CH— | CH$_3$ | H | CH$_3$ | |
| 89 | 3-Cl | —CH=CH— | CH$_3$ | H | CH$_3$ | |
| 90 | 4-Cl | —CH=CH— | CH$_3$ | H | CH$_3$ | |
| 91 | 2-Br | —CH=CH— | CH$_3$ | H | CH$_3$ | |
| 92 | 3-Br | —CH=CH— | CH$_3$ | H | CH$_3$ | |
| 93 | 4-Br | —CH=CH— | CH$_3$ | H | CH$_3$ | |
| 94 | 2,4-Cl$_2$ | —CH=CH— | CH$_3$ | H | CH$_3$ | |
| 95 | 2,6-Cl$_2$ | —CH=CH— | CH$_3$ | H | CH$_3$ | |
| 96 | 3,5-Cl$_2$ | —CH=CH— | CH$_3$ | H | CH$_3$ | |
| 97 | 2,4,6-Cl$_3$ | —CH=CH— | CH$_3$ | H | CH$_3$ | |
| 98 | 2-CH$_3$, 4-Cl | —CH=CH— | CH$_3$ | H | CH$_3$ | |
| 99 | 2-Cl, 4-CH$_3$ | —CH=CH— | CH$_3$ | H | CH$_3$ | |
| 100 | 2-CH$_3$ | —CH=CH— | CH$_3$ | H | CH$_3$ | |
| 101 | 3-CH$_3$ | —CH=CH— | CH$_3$ | H | CH$_3$ | |
| 102 | 4-CH$_3$ | —CH=CH— | CH$_3$ | H | CH$_3$ | |
| 103 | 4-C$_2$H$_5$ | —CH=CH— | CH$_3$ | H | CH$_3$ | |
| 104 | 4-i-C$_3$H$_7$ | —CH=CH— | CH$_3$ | H | CH$_3$ | |
| 105 | 4-t-C$_4$H$_9$ | —CH=CH— | CH$_3$ | H | CH$_3$ | |
| 106 | 2,4-(CH$_3$)$_2$ | —CH=CH— | CH$_3$ | H | CH$_3$ | |
| 107 | 2,6-(CH$_3$)$_2$ | —CH=CH— | CH$_3$ | H | CH$_3$ | |
| 108 | 2,4,6-(CH$_3$)$_3$ | —CH=CH— | CH$_3$ | H | CH$_3$ | |
| 109 | 2-OCH$_3$, 4-CH$_3$ | —CH=CH— | CH$_3$ | H | CH$_3$ | |
| 110 | 4-OCH$_3$, 2-CH$_3$ | —CH=CH— | CH$_3$ | H | CH$_3$ | |
| 111 | 2-OCH$_3$ | —CH=CH— | CH$_3$ | H | CH$_3$ | |
| 112 | 3-OCH$_3$ | —CH=CH— | CH$_3$ | H | CH$_3$ | |
| 113 | 4-OCH$_3$ | —CH=CH— | CH$_3$ | H | CH$_3$ | |
| 114 | 4-OC$_2$H$_5$ | —CH=CH— | CH$_3$ | H | CH$_3$ | |
| 115 | 4-O-i-C$_3$H$_7$ | —CH=CH— | CH$_3$ | H | CH$_3$ | |
| 116 | 2-CF$_3$ | —CH=CH— | CH$_3$ | H | CH$_3$ | |
| 117 | 3-CF$_3$ | —CH=CH— | CH$_3$ | H | CH$_3$ | |
| 118 | 4-CF$_3$ | —CH=CH— | CH$_3$ | H | CH$_3$ | |
| 119 | 2-CN | —CH=CH— | CH$_3$ | H | CH$_3$ | |
| 120 | 4-CN | —CH=CH— | CH$_3$ | H | CH$_3$ | |
| 121 | 3-NO$_2$ | —CH=CH— | CH$_3$ | H | CH$_3$ | |
| 122 | 4-NO$_2$ | —CH=CH— | CH$_3$ | H | CH$_3$ | |
| 123 | 4-C$_6$H$_5$ | —CH=CH— | CH$_3$ | H | CH$_3$ | |
| 124 | H | —CH$_2$—CH$_2$— | CH$_3$ | H | CH$_3$ | |
| 125 | 2-F | —CH$_2$—CH$_2$— | CH$_3$ | H | CH$_3$ | |
| 126 | 3-F | —CH$_2$—CH$_2$— | CH$_3$ | H | CH$_3$ | |
| 127 | 4-F | —CH$_2$—CH$_2$— | CH$_3$ | H | CH$_3$ | |
| 128 | 2-Cl, 6-F | —CH$_2$—CH$_2$— | CH$_3$ | H | CH$_3$ | |
| 129 | 2-Cl | —CH$_2$—CH$_2$— | CH$_3$ | H | CH$_3$ | |
| 130 | 3-Cl | —CH$_2$—CH$_2$— | CH$_3$ | H | CH$_3$ | |
| 131 | 4-Cl | —CH$_2$—CH$_2$— | CH$_3$ | H | CH$_3$ | |
| 132 | 2-Br | —CH$_2$—CH$_2$— | CH$_3$ | H | CH$_3$ | |
| 133 | 3-Br | —CH$_2$—CH$_2$— | CH$_3$ | H | CH$_3$ | |
| 134 | 4-Br | —CH$_2$—CH$_2$— | CH$_3$ | H | CH$_3$ | |
| 135 | 2,4-Cl$_2$ | —CH$_2$—CH$_2$— | CH$_3$ | H | CH$_3$ | |
| 136 | 2,6-Cl$_2$ | —CH$_2$—CH$_2$— | CH$_3$ | H | CH$_3$ | |
| 137 | 3,5-Cl$_2$ | —CH$_2$—CH$_2$— | CH$_3$ | H | CH$_3$ | |
| 138 | 2,4,6-Cl$_3$ | —CH$_2$—CH$_2$— | CH$_3$ | H | CH$_3$ | |
| 139 | 2-Cl, 4-CH$_3$ | —CH$_2$—CH$_2$— | CH$_3$ | H | CH$_3$ | |
| 140 | 2-CH$_3$, 4-Cl | —CH$_2$—CH$_2$— | CH$_3$ | H | CH$_3$ | |
| 141 | 2-CH$_3$ | —CH$_2$—CH$_2$— | CH$_3$ | H | CH$_3$ | |
| 142 | 3-CH$_3$ | —CH$_2$—CH$_2$— | CH$_3$ | H | CH$_3$ | |
| 143 | 4-CH$_3$ | —CH$_2$—CH$_2$— | CH$_3$ | H | CH$_3$ | |
| 144 | 4-C$_2$H$_5$ | —CH$_2$—CH$_2$— | CH$_3$ | H | CH$_3$ | |
| 145 | 4-i-C$_3$H$_7$ | —CH$_2$—CH$_2$— | CH$_3$ | H | CH$_3$ | |
| 146 | 4-t-C$_4$H$_9$ | —CH$_2$—CH$_2$— | CH$_3$ | H | CH$_3$ | |
| 147 | 2,4-(CH$_3$)$_2$ | —CH$_2$—CH$_2$— | CH$_3$ | H | CH$_3$ | |
| 148 | 2,6-(CH$_3$)$_2$ | —CH$_2$—CH$_2$— | CH$_3$ | H | CH$_3$ | |
| 149 | 2,4,6-(CH$_3$)$_3$ | —CH$_2$—CH$_2$— | CH$_3$ | H | CH$_3$ | |
| 150 | 2-OCH$_3$, 4-CH$_3$ | —CH$_2$—CH$_2$— | CH$_3$ | H | CH$_3$ | |
| 151 | 4-OCH$_3$, 2-CH$_3$ | —CH$_2$—CH$_2$— | CH$_3$ | H | CH$_3$ | |
| 152 | 2-OCH$_3$ | —CH$_2$—CH$_2$— | CH$_3$ | H | CH$_3$ | |
| 153 | 3-OCH$_3$ | —CH$_2$—CH$_2$— | CH$_3$ | H | CH$_3$ | |
| 154 | 4-OCH$_3$ | —CH$_2$—CH$_2$— | CH$_3$ | H | CH$_3$ | |
| 155 | 4-OC$_2$H$_5$ | —CH$_2$—CH$_2$— | CH$_3$ | H | CH$_3$ | |
| 156 | 4-O-i-C$_3$H$_7$ | —CH$_2$—CH$_2$— | CH$_3$ | H | CH$_3$ | |
| 157 | 2-CF$_3$ | —CH$_2$—CH$_2$— | CH$_3$ | H | CH$_3$ | |

TABLE-continued $$\underset{X_m}{\text{(structure)}} \quad R^3OOC\diagdown_{C=N-N<R^1}^{R^2} \quad (I)$$

| Comp. no. | $X_m$ | Y | $R^1$ | $R^2$ | $R^3$ | M.p.(°C.) IR(cm$^{-1}$) |
|---|---|---|---|---|---|---|
| 158 | 3-CF$_3$ | —CH$_2$—CH$_2$— | CH$_3$ | H | CH$_3$ | |
| 159 | 4-CF$_3$ | —CH$_2$—CH$_2$— | CH$_3$ | H | CH$_3$ | |
| 160 | 2-CN | —CH$_2$—CH$_2$— | CH$_3$ | H | CH$_3$ | |
| 161 | 4-CN | —CH$_2$—CH$_2$— | CH$_3$ | H | CH$_3$ | |
| 162 | 3-NO$_2$ | —CH$_2$—CH$_2$— | CH$_3$ | H | CH$_3$ | |
| 163 | 4-NO$_2$ | —CH$_2$—CH$_2$— | CH$_3$ | H | CH$_3$ | |
| 164 | 4-C$_6$H$_5$ | —CH$_2$—CH$_2$— | CH$_3$ | H | CH$_3$ | |
| 165 | H | ethynylene | CH$_3$ | H | CH$_3$ | |
| 166 | 2-F | ethynylene | CH$_3$ | H | CH$_3$ | |
| 167 | 2-Cl | ethynylene | CH$_3$ | H | CH$_3$ | |
| 168 | 2-Br | ethynylene | CH$_3$ | H | CH$_3$ | |
| 169 | 4-Br | ethynylene | CH$_3$ | H | CH$_3$ | |
| 170 | 2-CH$_3$ | ethynylene | CH$_3$ | H | CH$_3$ | |
| 171 | 4-CH$_3$ | ethynylene | CH$_3$ | H | CH$_3$ | |
| 172 | 2-OCH$_3$ | ethynylene | CH$_3$ | H | CH$_3$ | |
| 173 | 4-CF$_3$ | ethynylene | CH$_3$ | H | CH$_3$ | |
| 174 | 2-NO$_2$ | ethynylene | CH$_3$ | H | CH$_3$ | |
| 175 | H | O | CH$_3$ | H | CH$_3$ | |
| 176 | 2-F | O | CH$_3$ | H | CH$_3$ | |
| 177 | 2-Cl | O | CH$_3$ | H | CH$_3$ | |
| 178 | 2-Br | O | CH$_3$ | H | CH$_3$ | |
| 179 | 4-Br | O | CH$_3$ | H | CH$_3$ | |
| 180 | 4-Cl | O | CH$_3$ | H | CH$_3$ | |
| 181 | 2-CH$_3$ | O | CH$_3$ | H | CH$_3$ | |
| 182 | 4-CH$_3$ | O | CH$_3$ | H | CH$_3$ | |
| 183 | 2-OCH$_3$ | O | CH$_3$ | H | CH$_3$ | |
| 184 | 4-OCH$_3$ | O | CH$_3$ | H | CH$_3$ | |
| 185 | 4-C$_6$H$_5$ | O | CH$_3$ | H | CH$_3$ | |
| 186 | H | —CH$_2$O— | H | H | H | |
| 187 | H | —OCH$_2$— | H | H | H | |
| 188 | 4-OCH$_2$—C$_6$H$_5$ | —CH$_2$O— | CH$_3$ | H | CH$_3$ | |
| 189 | 4-OCH$_2$—C$_6$H$_5$ | —OCH$_2$— | CH$_3$ | H | CH$_3$ | |
| 190 | 4-OC$_6$H$_5$ | —CH$_2$O— | CH$_3$ | H | CH$_3$ | |
| 191 | 4-OC$_6$H$_5$ | —OCH$_2$— | CH$_3$ | H | CH$_3$ | |
| 192 | 4-O-(2-Cl-C$_6$H$_4$) | —CH$_2$O— | CH$_3$ | H | CH$_3$ | |
| 193 | 4-O-(2,4-Cl$_2$-C$_6$H$_3$) | —CH$_2$O— | CH$_3$ | H | CH$_3$ | |
| 194 | 4-O-(2-CH$_3$-C$_6$H$_4$) | —CH$_2$O— | CH$_3$ | H | CH$_3$ | |
| 195 | 3-OCH$_2$—C$_6$H$_5$ | —CH$_2$O— | CH$_3$ | H | CH$_3$ | |
| 196 | 3-OCH$_2$-(2-Cl-C$_6$H$_4$) | —CH$_2$O— | CH$_3$ | H | CH$_3$ | |

TABLE-continued

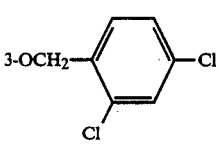
(I)

| Comp. no. | $X_m$ | Y | $R^1$ | $R^2$ | $R^3$ | M.p.(°C.) IR(cm$^{-1}$) |
|---|---|---|---|---|---|---|
| 197 | 3-OCH$_2$-(2,4-dichlorophenyl) | —CH$_2$O— | CH$_3$ | H | CH$_3$ | |
| 198 | 3-OCH$_2$-(2-fluorophenyl) | —CH$_2$O— | CH$_3$ | H | CH$_3$ | |
| 199 | 3-OCH$_2$-(4-bromophenyl) | —CH$_2$O— | CH$_3$ | H | CH$_3$ | |
| 200 | 3-OCH$_2$-(2-methylphenyl) | —CH$_2$O— | CH$_3$ | H | CH$_3$ | |
| 201 | 3-OC$_6$H$_5$ | —CH$_2$O— | CH$_3$ | H | CH$_3$ | |
| 202 | 3-O-(2-chlorophenyl) | —CH$_2$O— | CH$_3$ | H | CH$_3$ | |
| 203 | 3-O-(2,4-dichlorophenyl) | —CH$_2$O— | CH$_3$ | H | CH$_3$ | |
| 204 | 3-O-(2-fluorophenyl) | —CH$_2$O— | CH$_3$ | H | CH$_3$ | |
| 205 | 3-O-(4-bromophenyl) | —CH$_2$O— | CH$_3$ | H | CH$_3$ | |
| 206 | 3-O-(2-methylphenyl) | —CH$_2$O— | CH$_3$ | H | CH$_3$ | |
| 207 | H | —CH$_2$O— | CH$_3$ | H | H | |
| 208 | H | —CH$_2$O— | CH$_3$ | H | C$_2$H$_5$ | |
| 209 | H | —CH$_2$O— | CH$_3$ | H | C$_3$H$_7$ | |

TABLE-continued $$\underset{X_m}{\overset{R^3OOC}{\bigcirc}}\overset{N}{\underset{Y}{\bigcirc}}\overset{R^1}{\underset{R^2}{N}}$$ (I)

| Comp. no. | $X_m$ | Y | $R^1$ | $R^2$ | $R^3$ | M.p.(°C.) IR(cm$^{-1}$) |
|---|---|---|---|---|---|---|
| 210 | H | —CH$_2$O— | CH$_3$ | H | i-C$_3$H$_7$ | |
| 211 | H | —CH$_2$O— | CH$_3$ | H | n-C$_4$H$_9$ | |
| 212 | H | —OCH$_2$— | CH$_3$ | H | H | |
| 213 | H | —OCH$_2$— | CH$_3$ | H | C$_2$H$_5$ | |
| 214 | H | —OCH$_2$— | CH$_3$ | H | i-C$_3$H$_7$ | |
| 215 | H | —OCH$_2$— | CH$_3$ | H | n-C$_4$H$_9$ | |
| 216 | H | —CH$_2$O— | CH$_3$ | CH$_3$ | CH$_3$ | |
| 217 | 2-F | —CH$_2$O— | CH$_3$ | CH$_3$ | CH$_3$ | |
| 218 | 3-F | —CH$_2$O— | CH$_3$ | CH$_3$ | CH$_3$ | |
| 219 | 4-F | —CH$_2$O— | CH$_3$ | CH$_3$ | CH$_3$ | |
| 220 | 2-Cl, 6-F | —CH$_2$O— | CH$_3$ | CH$_3$ | CH$_3$ | |
| 221 | 2-Cl | —CH$_2$O— | CH$_3$ | CH$_3$ | CH$_3$ | 2945, 1693, 1556, 1488, 1437, 1303, 1202, 1072, 1030, 752 |
| 222 | 3-Cl | —CH$_2$O— | CH$_3$ | CH$_3$ | CH$_3$ | |
| 223 | 4-Cl | —CH$_2$O— | CH$_3$ | CH$_3$ | CH$_3$ | |
| 224 | 2-Br | —CH$_2$O— | CH$_3$ | CH$_3$ | CH$_3$ | |
| 225 | 3-Br | —CH$_2$O— | CH$_3$ | CH$_3$ | CH$_3$ | |
| 226 | 4-Br | —CH$_2$O— | CH$_3$ | CH$_3$ | CH$_3$ | |
| 227 | 2,4-Cl$_2$ | —CH$_2$O— | CH$_3$ | CH$_3$ | CH$_3$ | |
| 228 | 2,6-Cl$_2$ | —CH$_2$O— | CH$_3$ | CH$_3$ | CH$_3$ | |
| 229 | 3,5-Cl$_2$ | —CH$_2$O— | CH$_3$ | CH$_3$ | CH$_3$ | |
| 230 | 2,4,6-Cl$_3$ | —CH$_2$O— | CH$_3$ | CH$_3$ | CH$_3$ | |
| 231 | 2-Cl, 4-CH$_3$ | —CH$_2$O— | CH$_3$ | CH$_3$ | CH$_3$ | |
| 232 | 2-CH$_3$, 4-Cl | —CH$_2$O— | CH$_3$ | CH$_3$ | CH$_3$ | |
| 233 | 2-CH$_3$ | —CH$_2$O— | CH$_3$ | CH$_3$ | CH$_3$ | |
| 234 | 3-CH$_3$ | —CH$_2$O— | CH$_3$ | CH$_3$ | CH$_3$ | |
| 235 | 4-CH$_3$ | —CH$_2$O— | CH$_3$ | CH$_3$ | CH$_3$ | |
| 236 | 4-C$_2$H$_5$ | —CH$_2$O— | CH$_3$ | CH$_3$ | CH$_3$ | |
| 237 | 4-i-C$_3$H$_7$ | —CH$_2$O— | CH$_3$ | CH$_3$ | CH$_3$ | |
| 238 | 4-t-C$_4$H$_9$ | —CH$_2$O— | CH$_3$ | CH$_3$ | CH$_3$ | |
| 239 | 2,4-(CH$_3$)$_2$ | —CH$_2$O— | CH$_3$ | CH$_3$ | CH$_3$ | |
| 240 | 2,6-(CH$_3$)$_2$ | —CH$_2$O— | CH$_3$ | CH$_3$ | CH$_3$ | |
| 241 | 2,4,6-(CH$_3$)$_3$ | —CH$_2$O— | CH$_3$ | CH$_3$ | CH$_3$ | |
| 242 | 2-OCH$_3$, 4-CH$_3$ | —CH$_2$O— | CH$_3$ | CH$_3$ | CH$_3$ | |
| 243 | 4-OCH$_3$, 2-CH$_3$ | —CH$_2$O— | CH$_3$ | CH$_3$ | CH$_3$ | |
| 244 | 2-OCH$_3$ | —CH$_2$O— | CH$_3$ | CH$_3$ | CH$_3$ | |
| 245 | 3-OCH$_3$ | —CH$_2$O— | CH$_3$ | CH$_3$ | CH$_3$ | |
| 246 | 4-OCH$_3$ | —CH$_2$O— | CH$_3$ | CH$_3$ | CH$_3$ | |
| 247 | 4-OC$_2$H$_5$ | —CH$_2$O— | CH$_3$ | CH$_3$ | CH$_3$ | |
| 248 | 4-O-i-C$_3$H$_7$ | —CH$_2$O— | CH$_3$ | CH$_3$ | CH$_3$ | |
| 249 | 2-CF$_3$ | —CH$_2$O— | CH$_3$ | CH$_3$ | CH$_3$ | |
| 250 | 3-CF$_3$ | —CH$_2$O— | CH$_3$ | CH$_3$ | CH$_3$ | |
| 251 | 4-CF$_3$ | —CH$_2$O— | CH$_3$ | CH$_3$ | CH$_3$ | |
| 252 | 2-CN | —CH$_2$O— | CH$_3$ | CH$_3$ | CH$_3$ | |
| 253 | 4-CN | —CH$_2$O— | CH$_3$ | CH$_3$ | CH$_3$ | |
| 254 | 3-NO$_2$ | —CH$_2$O— | CH$_3$ | CH$_3$ | CH$_3$ | |
| 255 | 4-NO$_2$ | —CH$_2$O— | CH$_3$ | CH$_3$ | CH$_3$ | |
| 256 | 4-C$_6$H$_5$ | —CH$_2$O— | CH$_3$ | CH$_3$ | CH$_3$ | |
| 257 | H | —OCH$_2$— | CH$_3$ | CH$_3$ | CH$_3$ | |
| 258 | 2-F | —OCH$_2$— | CH$_3$ | CH$_3$ | CH$_3$ | |
| 259 | 3-F | —OCH$_2$— | CH$_3$ | CH$_3$ | CH$_3$ | |
| 260 | 4-F | —OCH$_2$— | CH$_3$ | CH$_3$ | CH$_3$ | |
| 261 | 2-Cl, 6-F | —OCH$_2$— | CH$_3$ | CH$_3$ | CH$_3$ | |
| 262 | 2-Cl | —OCH$_2$— | CH$_3$ | CH$_3$ | CH$_3$ | |
| 263 | 3-Cl | —OCH$_2$— | CH$_3$ | CH$_3$ | CH$_3$ | |
| 264 | 4-Cl | —OCH$_2$— | CH$_3$ | CH$_3$ | CH$_3$ | 2930, 1682, 1554, 1490, 1231, 1209, 1073, 1026, 824 |
| 265 | 2-Br | —OCH$_2$— | CH$_3$ | CH$_3$ | CH$_3$ | |
| 266 | 3-Br | —OCH$_2$— | CH$_3$ | CH$_3$ | CH$_3$ | |
| 267 | 4-Br | —OCH$_2$— | CH$_3$ | CH$_3$ | CH$_3$ | |
| 268 | 2,4-Cl$_2$ | —OCH$_2$— | CH$_3$ | CH$_3$ | CH$_3$ | |
| 269 | 2,6-Cl$_2$ | —OCH$_2$— | CH$_3$ | CH$_3$ | CH$_3$ | |
| 270 | 3,5-Cl$_2$ | —OCH$_2$— | CH$_3$ | CH$_3$ | CH$_3$ | |
| 271 | 2,4,6-Cl$_3$ | —OCH$_2$— | CH$_3$ | CH$_3$ | CH$_3$ | |
| 272 | 2-Cl, 4-CH$_3$ | —OCH$_2$— | CH$_3$ | CH$_3$ | CH$_3$ | |
| 273 | 2-CH$_3$, 4-Cl | —OCH$_2$— | CH$_3$ | CH$_3$ | CH$_3$ | |
| 274 | 2-CH$_3$ | —OCH$_2$— | CH$_3$ | CH$_3$ | CH$_3$ | |
| 275 | 3-CH$_3$ | —OCH$_2$— | CH$_3$ | CH$_3$ | CH$_3$ | |
| 276 | 4-CH$_3$ | —OCH$_2$— | CH$_3$ | CH$_3$ | CH$_3$ | 3420, 2950, 1681, 1555, 1507, 1438, 1303, 1223, 1026, 813 |
| 277 | 4-C$_2$H$_5$ | —OCH$_2$— | CH$_3$ | CH$_3$ | CH$_3$ | |

TABLE-continued

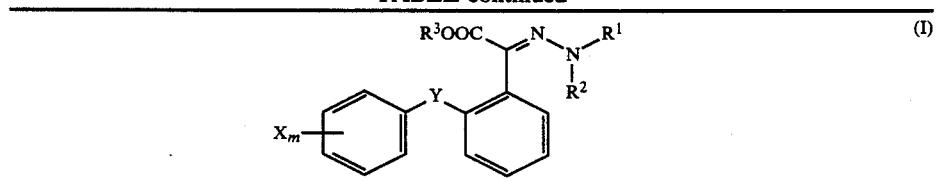

| Comp. no. | $X_m$ | Y | $R^1$ | $R^2$ | $R^3$ | M.p.(°C.) | IR(cm$^{-1}$) |
|---|---|---|---|---|---|---|---|
| 278 | 4-i-$C_3H_7$ | —$OCH_2$— | $CH_3$ | $CH_3$ | $CH_3$ | | |
| 279 | 4-t-$C_4H_9$ | —$OCH_2$— | $CH_3$ | $CH_3$ | $CH_3$ | | |
| 280 | 2,4-$(CH_3)_2$ | —$OCH_2$— | $CH_3$ | $CH_3$ | $CH_3$ | | |
| 281 | 2,6-$(CH_3)_2$ | —$OCH_2$— | $CH_3$ | $CH_3$ | $CH_3$ | | |
| 282 | 2,4,6-$(CH_3)_3$ | —$OCH_2$— | $CH_3$ | $CH_3$ | $CH_3$ | | |
| 283 | 2-$OCH_3$, 4-$CH_3$ | —$OCH_2$— | $CH_3$ | $CH_3$ | $CH_3$ | | |
| 284 | 4-$OCH_3$, 2-$CH_3$ | —$OCH_2$— | $CH_3$ | $CH_3$ | $CH_3$ | | |
| 285 | 2-$OCH_3$ | —$OCH_2$— | $CH_3$ | $CH_3$ | $CH_3$ | | |
| 286 | 3-$OCH_3$ | —$OCH_2$— | $CH_3$ | $CH_3$ | $CH_3$ | | |
| 287 | 4-$OCH_3$ | —$OCH_2$— | $CH_3$ | $CH_3$ | $CH_3$ | | |
| 288 | 4-$OC_2H_5$ | —$OCH_2$— | $CH_3$ | $CH_3$ | $CH_3$ | | |
| 289 | 4-O-$iC_3H_7$ | —$OCH_2$— | $CH_3$ | $CH_3$ | $CH_3$ | | |
| 290 | 2-$CF_3$ | —$OCH_2$— | $CH_3$ | $CH_3$ | $CH_3$ | | |
| 291 | 3-$CF_3$ | —$OCH_2$— | $CH_3$ | $CH_3$ | $CH_3$ | | |
| 292 | 4-$CF_3$ | —$OCH_2$— | $CH_3$ | $CH_3$ | $CH_3$ | | |
| 293 | 2-CN | —$OCH_2$— | $CH_3$ | $CH_3$ | $CH_3$ | | |
| 294 | 4-CN | —$OCH_2$— | $CH_3$ | $CH_3$ | $CH_3$ | | |
| 295 | 3-$NO_2$ | —$OCH_2$— | $CH_3$ | $CH_3$ | $CH_3$ | | |
| 296 | 4-$NO_2$ | —$OCH_2$— | $CH_3$ | $CH_3$ | $CH_3$ | | |
| 297 | 4-$C_6H_5$ | —$OCH_2$— | $CH_3$ | $CH_3$ | $CH_3$ | | |
| 298 | H | —$CO_2$—$CH_2$— | $CH_3$ | H | $CH_3$ | | |
| 299 | 2-F | —$CO_2$—$CH_2$— | $CH_3$ | H | $CH_3$ | | |
| 300 | 3-F | —$CO_2$—$CH_2$— | $CH_3$ | H | $CH_3$ | | |
| 301 | 4-F | —$CO_2$—$CH_2$— | $CH_3$ | H | $CH_3$ | | |
| 302 | 2-Cl, 6-F | —$CO_2$—$CH_2$— | $CH_3$ | H | $CH_3$ | | |
| 303 | 2-Cl | —$CO_2$—$CH_2$— | $CH_3$ | H | $CH_3$ | | |
| 304 | 3-Cl | —$CO_2$—$CH_2$— | $CH_3$ | H | $CH_3$ | | |
| 305 | 4-Cl | —$CO_2$—$CH_2$— | $CH_3$ | H | $CH_3$ | | |
| 306 | 2-Br | —$CO_2$—$CH_2$— | $CH_3$ | H | $CH_3$ | | |
| 307 | 3-Br | —$CO_2$—$CH_2$— | $CH_3$ | H | $CH_3$ | | |
| 308 | 4-Br | —$CO_2$—$CH_2$— | $CH_3$ | H | $CH_3$ | | |
| 309 | 2,4-$Cl_2$ | —$CO_2$—$CH_2$— | $CH_3$ | H | $CH_3$ | | |
| 310 | 2,6-$Cl_2$ | —$CO_2$—$CH_2$— | $CH_3$ | H | $CH_3$ | | |
| 311 | 3,5-$Cl_2$ | —$CO_2$—$CH_2$— | $CH_3$ | H | $CH_3$ | | |
| 312 | 2,4,6-$Cl_3$ | —$CO_2$—$CH_2$— | $CH_3$ | H | $CH_3$ | | |
| 313 | 2-Cl, 4-$CH_3$ | —$CO_2$—$CH_2$— | $CH_3$ | H | $CH_3$ | | |
| 314 | 2-$CH_3$, 4-Cl | —$CO_2$—$CH_2$— | $CH_3$ | H | $CH_3$ | | |
| 315 | 2-$CH_3$ | —$CO_2$—$CH_2$— | $CH_3$ | H | $CH_3$ | | |
| 316 | 3-$CH_3$ | —$CO_2$—$CH_2$— | $CH_3$ | H | $CH_3$ | | |
| 317 | 4-$CH_3$ | —$CO_2$—$CH_2$— | $CH_3$ | H | $CH_3$ | | |
| 318 | 4-$C_2H_5$ | —$CO_2$—$CH_2$— | $CH_3$ | H | $CH_3$ | | |
| 319 | 4-i-$C_3H_7$ | —$CO_2$—$CH_2$— | $CH_3$ | H | $CH_3$ | | |
| 320 | 4-t-$C_4H_9$ | —$CO_2$—$CH_2$— | $CH_3$ | H | $CH_3$ | | |
| 321 | 2,4-$(CH_3)_2$ | —$CO_2$—$CH_2$— | $CH_3$ | H | $CH_3$ | | |
| 322 | 2,6-$(CH_3)_2$ | —$CO_2$—$CH_2$— | $CH_3$ | H | $CH_3$ | | |
| 323 | 2,4,6-$(CH_3)_3$ | —$CO_2$—$CH_2$— | $CH_3$ | H | $CH_3$ | | |
| 324 | 2-$OCH_3$, 4-$CH_3$ | —$CO_2$—$CH_2$— | $CH_3$ | H | $CH_3$ | | |
| 325 | 4-$OCH_3$, 2-$CH_3$ | —$CO_2$—$CH_2$— | $CH_3$ | H | $CH_3$ | | |
| 326 | 2-$OCH_3$ | —$CO_2$—$CH_2$— | $CH_3$ | H | $CH_3$ | | |
| 327 | 3-$OCH_3$ | —$CO_2$—$CH_2$— | $CH_3$ | H | $CH_3$ | | |
| 328 | 4-$OCH_3$ | —$CO_2$—$CH_2$— | $CH_3$ | H | $CH_3$ | | |
| 329 | 4-$OC_2H_5$ | —$CO_2$—$CH_2$— | $CH_3$ | H | $CH_3$ | | |
| 330 | 4-O-i-$C_3H_7$ | —$CO_2$—$CH_2$— | $CH_3$ | H | $CH_3$ | | |
| 331 | 2-$CF_3$ | —$CO_2$—$CH_2$— | $CH_3$ | H | $CH_3$ | | |
| 332 | 3-$CF_3$ | —$CO_2$—$CH_2$— | $CH_3$ | H | $CH_3$ | | |
| 333 | 4-$CF_3$ | —$CO_2$—$CH_2$— | $CH_3$ | H | $CH_3$ | | |
| 334 | 2-CN | —$CO_2$—$CH_2$— | $CH_3$ | H | $CH_3$ | | |
| 335 | 4-CN | —$CO_2$—$CH_2$— | $CH_3$ | H | $CH_3$ | | |
| 336 | 3-$NO_2$ | —$CO_2$—$CH_2$— | $CH_3$ | H | $CH_3$ | | |
| 337 | 4-$NO_2$ | —$CO_2$—$CH_2$— | $CH_3$ | H | $CH_3$ | | |
| 338 | 4-$C_6H_5$ | —$CO_2$—$CH_2$— | $CH_3$ | H | $CH_3$ | | |
| 339 | H | —CH=CH— | $CH_3$ | $CH_3$ | $CH_3$ | | |
| 340 | H | —$CH_2$—$CH_2$— | $CH_3$ | $CH_3$ | $CH_3$ | | |
| 341 | H | ethynylene | $CH_3$ | $CH_3$ | $CH_3$ | | |
| 342 | H | O | $CH_3$ | $CH_3$ | $CH_3$ | | |
| 343 | H | —$CO_2$—$CH_2$— | $CH_3$ | $CH_3$ | $CH_3$ | | |
| 344 | H | —$CH_2O$— | $C_2H_5$ | H | $CH_3$ | | |
| 345 | H | —$CH_2O$— | $C_3H_7$ | H | $CH_3$ | | |
| 346 | H | —$CH_2O$— | i-$C_3H_7$ | H | $CH_3$ | | |
| 347 | H | —$CH_2O$— | n-$C_4H_9$ | H | $CH_3$ | | |
| 348 | H | —$CH_2O$— | i-$C_4H_9$ | H | $CH_3$ | | |

TABLE-continued $$\text{(I)}$$

Structure: $X_m$-phenyl-Y-phenyl-C(=N-N(R¹)(R²))-COOR³

| Comp. no. | $X_m$ | Y | R¹ | R² | R³ | M.p.(°C.) IR(cm⁻¹) |
|---|---|---|---|---|---|---|
| 349 | H | —CH₂O— | t-C₄H₉ | H | CH₃ | |
| 350 | H | —CH₂O— | C₅H₁₁ | H | CH₃ | |
| 351 | H | —OCH₂— | C₂H₅ | H | CH₃ | |
| 352 | H | —OCH₂— | C₃H₇ | H | CH₃ | |
| 353 | H | —OCH₂— | i-C₃H₇ | H | CH₃ | |
| 354 | H | —OCH₂— | n-C₄H₉ | H | CH₃ | |
| 355 | H | —OCH₂— | i-C₄H₉ | H | CH₃ | |
| 356 | H | —OCH₂— | t-C₄H₉ | H | CH₃ | |
| 357 | H | —OCH₂— | C₅H₁₁ | H | CH₃ | |
| 358 | H | —CH₂O— | C₂H₅ | C₂H₅ | CH₃ | |
| 359 | H | —CO₂—CH₂— | C₂H₅ | H | CH₃ | |
| 360 | H | —CO₂—CH₂— | C₃H₇ | H | CH₃ | |
| 361 | H | —CO—NH— | CH₃ | CH₃ | CH₃ | |
| 362 | H | —CH₂—NH— | CH₃ | CH₃ | CH₃ | |
| 363 | H | —CO—NH— | C₂H₅ | H | CH₃ | |
| 364 | H | —CH₂—NH— | C₂H₅ | H | CH₃ | |
| 365 | H | —CO—NH— | CH₃ | H | CH₃ | |
| 366 | 2-F | —CO—NH— | CH₃ | H | CH₃ | |
| 367 | 3-F | —CO—NH— | CH₃ | H | CH₃ | |
| 368 | 4-F | —CO—NH— | CH₃ | H | CH₃ | |
| 369 | 2-Cl, 6-F | —CO—NH— | CH₃ | H | CH₃ | |
| 370 | 2-Cl | —CO—NH— | CH₃ | H | CH₃ | |
| 371 | 3-Cl | —CO—NH— | CH₃ | H | CH₃ | |
| 372 | 4-Cl | —CO—NH— | CH₃ | H | CH₃ | |
| 373 | 2-Br | —CO—NH— | CH₃ | H | CH₃ | |
| 374 | 3-Br | —CO—NH— | CH₃ | H | CH₃ | |
| 375 | 4-Br | —CO—NH— | CH₃ | H | CH₃ | |
| 376 | 2,4-Cl₂ | —CO—NH— | CH₃ | H | CH₃ | |
| 377 | 2,6-Cl₂ | —CO—NH— | CH₃ | H | CH₃ | |
| 378 | 3,5-Cl₂ | —CO—NH— | CH₃ | H | CH₃ | |
| 379 | 2,4,6-Cl₃ | —CO—NH— | CH₃ | H | CH₃ | |
| 380 | 2-Cl, 4-CH₃ | —CO—NH— | CH₃ | H | CH₃ | |
| 381 | 2-CH₃, 4-Cl | —CO—NH— | CH₃ | H | CH₃ | |
| 382 | 2-CH₃ | —CO—NH— | CH₃ | H | CH₃ | |
| 383 | 3-CH₃ | —CO—NH— | CH₃ | H | CH₃ | |
| 384 | 4-CH₃ | —CO—NH— | CH₃ | H | CH₃ | |
| 385 | 4-C₂H₅ | —CO—NH— | CH₃ | H | CH₃ | |
| 386 | 4-i-C₃H₇ | —CO—NH— | CH₃ | H | CH₃ | |
| 387 | 4-t-C₄H₉ | —CO—NH— | CH₃ | H | CH₃ | |
| 388 | 2,4-(CH₃)₂ | —CO—NH— | CH₃ | H | CH₃ | |
| 389 | 2,6-(CH₃)₂ | —CO—NH— | CH₃ | H | CH₃ | |
| 390 | 2,4,6-(CH₃)₃ | —CO—NH— | CH₃ | H | CH₃ | |
| 391 | 2-OCH₃, 4-CH₃ | —CO—NH— | CH₃ | H | CH₃ | |
| 392 | 4-OCH₃, 2-CH₃ | —CO—NH— | CH₃ | H | CH₃ | |
| 393 | 2-OCH₃ | —CO—NH— | CH₃ | H | CH₃ | |
| 394 | 3-OCH₃ | —CO—NH— | CH₃ | H | CH₃ | |
| 395 | 4-OCH₃ | —CO—NH— | CH₃ | H | CH₃ | |
| 396 | 4-OC₂H₅ | —CO—NH— | CH₃ | H | CH₃ | |
| 397 | 4-O-i-C₃H₇ | —CO—NH— | CH₃ | H | CH₃ | |
| 398 | 2-CF₃ | —CO—NH— | CH₃ | H | CH₃ | |
| 399 | 3-CF₃ | —CO—NH— | CH₃ | H | CH₃ | |
| 400 | 4-CF₃ | —CO—NH— | CH₃ | H | CH₃ | |
| 401 | 2-CN | —CO—NH— | CH₃ | H | CH₃ | |
| 402 | 4-CN | —CO—NH— | CH₃ | H | CH₃ | |
| 403 | 3-NO₂ | —CO—NH— | CH₃ | H | CH₃ | |
| 404 | 4-NO₂ | —CO—NH— | CH₃ | H | CH₃ | |
| 405 | 4-C₆H₅ | —CO—NH— | CH₃ | H | CH₃ | |
| 406 | H | —CH₂—NH— | CH₃ | H | CH₃ | |
| 407 | 2-F | —CH₂—NH— | CH₃ | H | CH₃ | |
| 408 | 3-F | —CH₂—NH— | CH₃ | H | CH₃ | |
| 409 | 4-F | —CH₂—NH— | CH₃ | H | CH₃ | |
| 410 | 2-Cl, 6-F | —CH₂—NH— | CH₃ | H | CH₃ | |
| 411 | 2-Cl | —CH₂—NH— | CH₃ | H | CH₃ | |
| 412 | 3-Cl | —CH₂—NH— | CH₃ | H | CH₃ | |
| 413 | 4-Cl | —CH₂—NH— | CH₃ | H | CH₃ | |
| 414 | 2-Br | —CH₂—NH— | CH₃ | H | CH₃ | |
| 415 | 3-Br | —CH₂—NH— | CH₃ | H | CH₃ | |
| 416 | 4-Br | —CH₂—NH— | CH₃ | H | CH₃ | |
| 417 | 2,4-Cl₂ | —CH₂—NH— | CH₃ | H | CH₃ | |
| 418 | 2,6-Cl₂ | —CH₂—NH— | CH₃ | H | CH₃ | |
| 419 | 3,5-Cl₂ | —CH₂—NH— | CH₃ | H | CH₃ | |

TABLE-continued $$\text{(I)}$$

Structure: $X_m$—(phenyl)—Y—(phenyl)—C(=N—N(R$^1$)R$^2$)—COOR$^3$

| Comp. no. | $X_m$ | Y | $R^1$ | $R^2$ | $R^3$ | M.p.(°C.) IR(cm$^{-1}$) |
|---|---|---|---|---|---|---|
| 420 | 2,4,6-Cl$_3$ | —CH$_2$—NH— | CH$_3$ | H | CH$_3$ | |
| 421 | 2-Cl, 4-CH$_3$ | —CH$_2$—NH— | CH$_3$ | H | CH$_3$ | |
| 422 | 2-CH$_3$, 4-Cl | —CH$_2$—NH— | CH$_3$ | H | CH$_3$ | |
| 423 | 2-CH$_3$ | —CH$_2$—NH— | CH$_3$ | H | CH$_3$ | |
| 424 | 3-CH$_3$ | —CH$_2$—NH— | CH$_3$ | H | CH$_3$ | |
| 425 | 4-CH$_3$ | —CH$_2$—NH— | CH$_3$ | H | CH$_3$ | |
| 426 | 4-C$_2$H$_5$ | —CH$_2$—NH— | CH$_3$ | H | CH$_3$ | |
| 427 | 4-i-C$_3$H$_7$ | —CH$_2$—NH— | CH$_3$ | H | CH$_3$ | |
| 428 | 4-t-C$_4$H$_9$ | —CH$_2$—NH— | CH$_3$ | H | CH$_3$ | |
| 429 | 2,4-(CH$_3$)$_2$ | —CH$_2$—NH— | CH$_3$ | H | CH$_3$ | |
| 430 | 2,6-(CH$_3$)$_2$ | —CH$_2$—NH— | CH$_3$ | H | CH$_3$ | |
| 431 | 2,4,6-(CH$_3$)$_3$ | —CH$_2$—NH— | CH$_3$ | H | CH$_3$ | |
| 432 | 2-OCH$_3$, 4-CH$_3$ | —CH$_2$—NH— | CH$_3$ | H | CH$_3$ | |
| 433 | 4-OCH$_3$, 2-CH$_3$ | —CH$_2$—NH— | CH$_3$ | H | CH$_3$ | |
| 434 | 2-OCH$_3$ | —CH$_2$—NH— | CH$_3$ | H | CH$_3$ | |
| 435 | 3-OCH$_3$ | —CH$_2$—NH— | CH$_3$ | H | CH$_3$ | |
| 436 | 4-OCH$_3$ | —CH$_2$—NH— | CH$_3$ | H | CH$_3$ | |
| 437 | 4-OC$_2$H$_5$ | —CH$_2$—NH— | CH$_3$ | H | CH$_3$ | |
| 438 | 4-O-i-C$_3$H$_7$ | —CH$_2$—NH— | CH$_3$ | H | CH$_3$ | |
| 439 | 2-CF$_3$ | —CH$_2$—NH— | CH$_3$ | H | CH$_3$ | |
| 440 | 3-CF$_3$ | —CH$_2$—NH— | CH$_3$ | H | CH$_3$ | |
| 441 | 4-CF$_3$ | —CH$_2$—NH— | CH$_3$ | H | CH$_3$ | |
| 442 | 2-CN | —CH$_2$—NH— | CH$_3$ | H | CH$_3$ | |
| 443 | 4-CN | —CH$_2$—NH— | CH$_3$ | H | CH$_3$ | |
| 444 | 3-NO$_2$ | —CH$_2$—NH— | CH$_3$ | H | CH$_3$ | |
| 445 | 4-NO$_2$ | —CH$_2$—NH— | CH$_3$ | H | CH$_3$ | |
| 446 | 4-C$_6$H$_5$ | —CH$_2$—NH— | CH$_3$ | H | CH$_3$ | |
| 447 | 2-Cl | —CH$_2$O— | H | H | CH$_3$ | 3418, 3295, 1718, 1565, 1491, 1435, 1340, 1226, 1029, 749 |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 30 is mixed with 10 parts by weight of N-methyl-α-pyrrolidone. A mixture is obtained which is suitable for application in the form of very fine drops.

II. 20 parts by weight of compound no. 42 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 30 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 42 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 30 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 42 is intimately mixed with 97 parts by weight of particulate kaolin. A dust is obtained containing 3% by weight of the active ingredient.

VII. 30 parts by weight of compound no. 30 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 422a is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 30 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide, 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

For comparison purposes, N-tridecyl-2,6-dimethylmorpholine (A) disclosed in DE-1,164,152 was used.

USE EXAMPLE 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of Plasmopara viticola. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 30 and 42, applied as 0.05% spray liquors, have a better fungicidal action (90%) than prior art comparative agent A (50%).

USE EXAMPLE 2

Action on *Pyricularia oryzae* (protective)

Leaves of pot-grown rice seedlings of the "Bahia" variety were sprayed to runoff with aqueous emulsions containing (dry basis) 80% of active ingredient and 20% of emulsifier, and inoculated 24 hours later with an aqueous spore suspension of *Pyricularia oryzae*. The plants were then set up in climatic cabinets at 22° to 24° C. and 95 to 99% relative humidity. The extent of fungus attack was assessed after 6 days.

The results show that active ingredient 42, applied as a 0.05% spray liquor, has a better fungicidal action (90%) than prior art comparative agent A (50%).

We claim:

1. Substituted hydrazones of the formula I

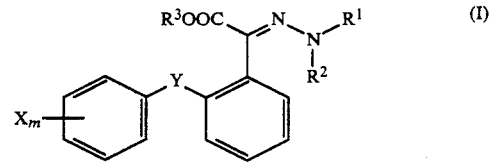

where
R$^1$, R$^2$ and R$^3$ are identical or different and each denotes hydrogen or alkyl of 1 to 5 carbon atoms,
X (m=1 to 5) is one or more identical or different substituents selected from the group consisting of halogen, cyano, trifluoromethyl, nitro, C$_1$–C$_4$-alkyl, C$_1$–C$_4$-alkoxy, phenyl, phenoxy, halophenoxy, C$_1$–C$_4$alkylphenoxy, benzyloxy, halobenzyloxy, C$_1$–C$_4$-alkylbenzyloxy, and hydrogen, and
Y is methyleneoxy, oxymethylene, ethylene, ethenylene, ethynylene, carboxymethylene, carbonylamino, methyleneamino or oxygen.

2. Compounds of the formula I as set forth in claim 1, where
X is hydrogen, 2-fluoro, 3-fluoro, 4-fluoro, 2-chloro-6-fluoro, 2-chloro, 3-chloro, 4-chloro, 2-bromo, 3-bromo, 4-bromo, 2,4-dichloro, 2,6-dichloro, 3,5-dichloro, 2,4,6-trichloro, 2-chloro-4-methyl, 2-methyl-4-chloro, 2-methyl, 3-methyl, 4-methyl, 4-ethyl, 4-isopropyl, 4-tert-butyl, 2,4-dimethyl, 2,6-dimethyl, 2,4,6-trimethyl, 2-methoxy-4-methyl, 4-methoxy-2-methyl, 2-methoxy, 3-methoxy, 4- methoxy, 4-ethoxy, 4-isopropoxy, 2-trifluoromethyl, 3-trifluoromethyl, 4-trifluoromethyl, 2-cyano, 4-cyano, 3-nitro, 4-nitro, 4-phenyl, 4-benzyloxy, 4-phenoxy, halophenoxy, 4-(2-chloro)-phenoxy, 4-(2,4-dichloro)-phenoxy, $C_1$-$C_4$-alkylphenoxy, 4-(2-methyl)-phenoxy, 3-benzyloxy, halobenzyloxy, 3-(2-chlor)-benzyloxy, 3-(2,4-dichloro)-benzyloxy, 3-(2-fluoro)-benzyloxy, 3-(4-bromo)-benzyloxy, $C_1$-$C_4$-alkylbenzyloxy, 3-(2-methyl)-benzyloxy, 3-phenoxy, 3-(2-chloro)-phenoxy, 3-(2,4-dichloro)-phenoxy, 3-(2-fluoro)-phenoxy, 3-(4-bromo)-phenoxy, or 3-(2-methyl)-phenoxy, $R^1$ is hydrogen, methyl, ethyl, n-propyl, isopropyl, n-butyl, sec-butyl, isobutyl, tert-butyl, n-pentyl or neopentyl, $R^2$ is hydrogen, methyl, ethyl, n-propyl, isopropyl, n-butyl, sec-butyl, isobutyl, tert-butyl, n-pentyl or neopentyl, $R^3$ is hydrogen, methyl, ethyl, isopropyl, n-butyl and Y is a —$CH_2O$—, —$OCH_2$—, —$CH_2$—$CH_2$—, —CH=CH—, —C≡C—, —$CO_2$—$CH_2$—, —CO—NH—, or —$CH_2$—NH— group or oxygen.

3. A fungicidal agent containing a substituted hydrazone of the formula I

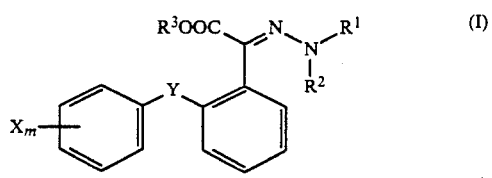

where $R^1$, $R^2$ and $R^3$ are identical or different and each denotes hydrogen or alkyl of 1 to 5 carbon atoms, X (m=1 to 5) is one or more identical or different substituents selected from the group consisting of halogen, cyano, trifluoromethyl, nitro, $C_1$-$C_4$-alkyl, $C_1$-$C_4$-alkoxy, phenyl, phenoxy, halophenoxy, $C_1$-$C_4$-alkylphenoxy, benzyloxy, halobenzyloxy, $C_1$-$C_4$-alkylbenzyloxy, and hydrogen, and Y is methyleneoxy, oxymethylene, ethylene, ethenylene, ethynylene, carboxymethylene, carbonylamino, methyleneamino or oxygen.

4. A compound as set forth in claim 1, where $R^1$ is methyl, $R^2$ is hydrogen, $R^3$ is methyl, $X_m$ is hydrogen and Y is methyleneoxy.

5. A compound as set forth in claim 1, where $R^1$ is methyl, $R^2$ is hydrogen, $R^3$ is methyl, $X_m$ is hydrogen and Y is oxymethylene.

6. A compound as set forth in claim 1, where $R^1$ is methyl, $R^2$ is hydrogen, $R^3$ is methyl, $X_m$ is 3-methoxy and Y is methyleneoxy.

7. A compound as set forth in claim 1, where $R^1$ is methyl, $R^2$ is methyl, $R^3$ is methyl, $X_m$ is 4-methyl and Y is oxymethylene.

8. A compound as set forth in claim 1, where $R^1$ and $R^3$ are methyl, $R^2$ is hydrogen, $X_m$ is 2-methyl and Y is oxymethylene.

* * * * *